(12) United States Patent
Beck et al.

(10) Patent No.: US 6,504,075 B2
(45) Date of Patent: Jan. 7, 2003

(54) SMALL CRYSTAL ZSM-5, ITS SYNTHESIS AND USE

(75) Inventors: Jeffrey S. Beck, Burlington; Carrie L. Kennedy, Turnersville; Wieslaw J. Roth, Sewell; David L. Stern, Mount Laurel, all of NJ (US)

(73) Assignee: ExxonMobil Oil Corporation, Fairfax, VA (US)

( * ) Notice: Subject to any disclaimer, the term of this patent is extended or adjusted under 35 U.S.C. 154(b) by 10 days.

(21) Appl. No.: 09/767,183

(22) Filed: Jan. 22, 2001

(65) Prior Publication Data

US 2001/0024635 A1 Sep. 27, 2001

Related U.S. Application Data

(63) Continuation of application No. 09/218,191, filed on Dec. 22, 1998, now Pat. No. 6,180,550.

(51) Int. Cl.⁷ .............................. C07C 5/52; C07C 5/22
(52) U.S. Cl. ........................................ 585/475; 585/481
(58) Field of Search ................................. 585/475, 481

(56) References Cited

U.S. PATENT DOCUMENTS

| | | | |
|---|---|---|---|
| 3,702,886 A | 11/1972 | Argauer et al. | 423/328 |
| 3,926,782 A | 12/1975 | Plank et al. | 208/135 |
| 3,968,024 A | 7/1976 | Gorring et al. | 208/111.15 |
| 4,060,568 A | 11/1977 | Rodewald | 585/640 |
| 4,151,189 A | 4/1979 | Rubin et al. | 260/448 |
| 4,379,027 A | 4/1983 | Klosek et al. | 203/32 |
| 4,526,879 A | 7/1985 | Dwyer et al. | 502/71 |
| 4,678,766 A | 7/1987 | Rosinski | 502/85 |
| 4,773,987 A | 9/1988 | Garwood et al. | 208/111 |
| 4,845,063 A | 7/1989 | Chu | 502/60 |
| 4,899,011 A | 2/1990 | Chu et al. | 585/481 |
| 5,240,892 A | 8/1993 | Klocke | 502/77 |
| 5,271,920 A | 12/1993 | Chang et al. | 423/700 |
| 5,369,071 A | 11/1994 | Degnan et al. | 502/71 |
| 5,614,079 A | 3/1997 | Farnos et al. | 208/27 |
| 5,705,726 A | 1/1998 | Abichandani et al. | 585/481 |
| 5,888,378 A | 3/1999 | Kowalski | 208/114 |
| 6,180,550 B1 * | 1/2001 | Beck et al. | 502/77 |

FOREIGN PATENT DOCUMENTS

| | | | |
|---|---|---|---|
| EP | 106552 A1 | 4/1984 | |
| EP | 306238 | 3/1989 | C01B/33/28 | cited by examiner

*Primary Examiner*—Steven P. Griffin
*Assistant Examiner*—Christina Ildebrando

(57) ABSTRACT

A synthetic porous crystalline material has the structure of ZSM-5 and a composition involving the molar relationship:

$$X_2O_3:(n)YO_2,$$

wherein X is a trivalent element; Y is a tetravalent element; and n is less than 25, and wherein the slope of the nitrogen sorption isotherm of the material at a partial pressure of nitrogen of 0.4 to 0.7 and a temperature 77° K is greater than 30. The material has a mesoporous surface area (MSA) greater than 45 m²/g and is useful as a catalyst in the liquid phase isomerization of xylene.

14 Claims, 1 Drawing Sheet

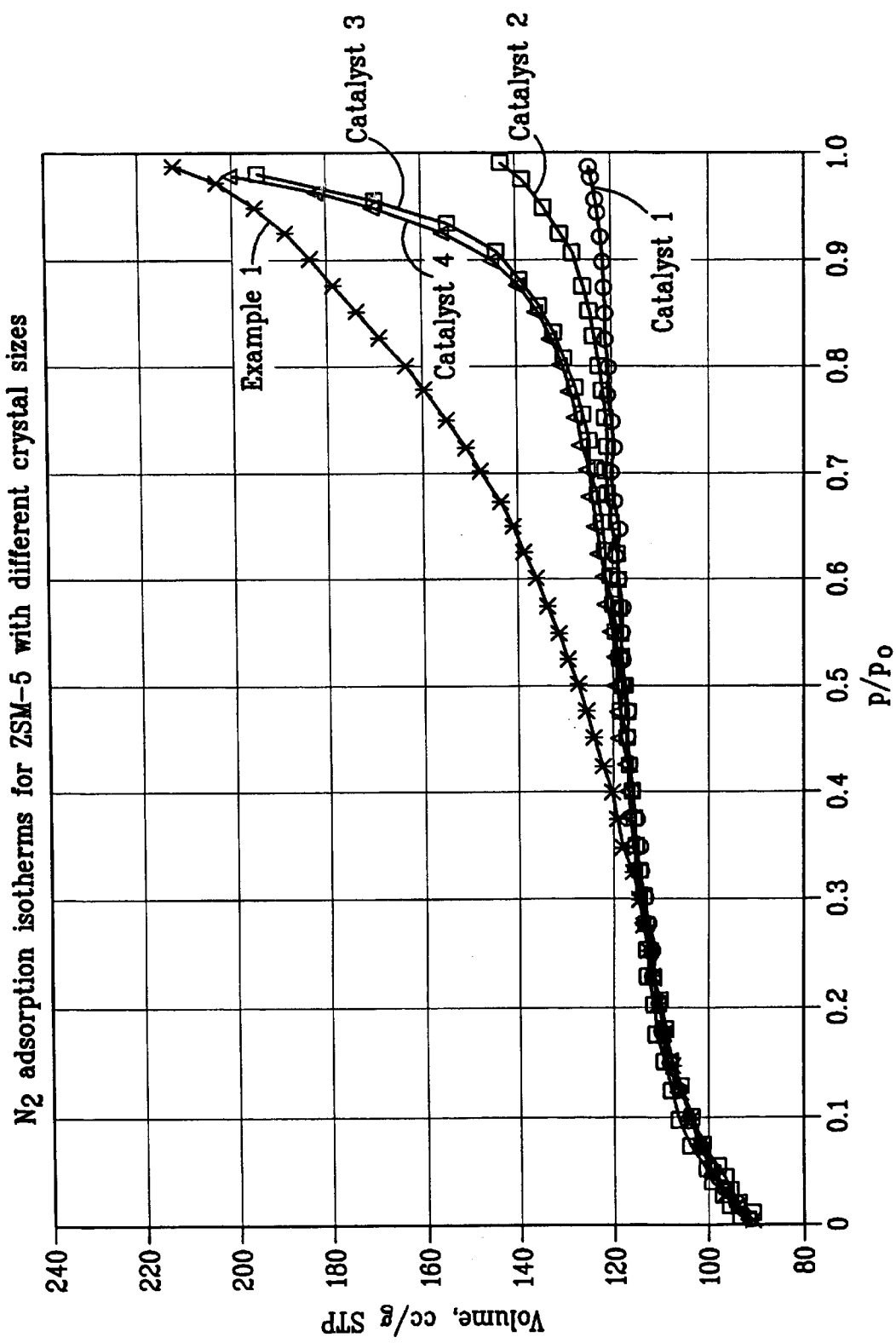
FIGURE
N₂ adsorption isotherms for ZSM-5 with different crystal sizes

SMALL CRYSTAL ZSM-5, ITS SYNTHESIS AND USE

This application is a continuation of Ser. No. 09/218,191 filed on Dec. 22, 1998, now U.S. Pat. No. 6,180,550.

FIELD OF THE INVENTION

This invention relates to small crystal ZSM-5, its synthesis and its use in catalytic processes, particularly xylene isomerization.

BACKGROUND OF THE INVENTION

ZSM-5 and its synthesis using tetrapropylammonium (TPA) cations as a directing agent are disclosed in U.S. Pat. No. 3,702,886. U.S. Pat. No. 3,926,782 discloses hydrocarbon conversion over ZSM-5 crystals having a crystal size of 0.005–0.1 micron synthesized in the presence of TPA cations.

U.S. Pat. No. 4,151,189 discloses that ZSM-5 can be synthesized in the presence of a primary amine having 2–9 carbon atoms, particularly n-propylamine. U.S. Pat. No. 5,369,071 discloses the use of n-propylamine in the synthesis of ZSM-5 with a silica to alumina ratio as low as 20.3 from a reaction mixture having a pH 10–14, an $OH^-/SiO_2$ ratio of 0.1–0.3, an $M/SiO_2$ ratio of 0.2–0.6 (where M is an alkali or alkaline earth metal) and an $H_2O/SiO_2$ ratio of 10–35.

EP-A-106552 teaches that ZSM-5 and ferrierite can be synthesized in the absence of an inorganic directing agent by using an amorphous granular silica-alumina as the source of silicon and aluminum. The resultant ZSM-5 is said to have a silica to alumina molar ratio of 15–100 but the only ZSM-5 product exemplified has a silica to alumina molar ratio of 58.8. EP-A-106552 fails to disclose the crystal size of the ZSM-5 produced.

EP-A-306238 discloses that ZSM-5 crystals having a platelet morphology with two dimensions of at least 0.05 micron, typically at least 0.1 micron, and a third dimension less than 0.02 micron can be synthesized from a non-organic synthesis mixture having at least 35 wt % solids and an $OH^-/SiO_2$ ratio of at least 0.11.

Other non-organic synthesis routes for ZSM-5 are known and commercially practiced and typically produce a material having a silica to alumina molar ratio of 20–30 and a crystal size of about 0.2–0.5 micron.

To date it has proved extremely difficult to produce ZSM-5 from reaction mixtures with silica to alumina molar ratios less than about 20, which could produce crystals with correspondingly lower framework silica to alumina molar ratio. Framework aluminum sites are responsible for the acid activity of zeolites, and it is desirable for many catalytic uses to be able to produce ZSM-5 with a framework silica to alumina molar ratio as low as possible. Similarly, for catalytic uses where rapid diffusion of reactants and products into and out of the zeolite is desirable, it is important to be able to produce ZSM-5 with a small crystal size, for example less than 0.1 micron.

The problem of producing ZSM-5 with a low silica to alumina molar ratio has been particularly pronounced in the case of small crystal materials. Thus to date small crystal ZSM-5, with a crystal size of less than 0.1 micron, has been obtained only with silica/alumina ratios higher than approximately 23:1.

The crystal size of a zeolite can be determined by direct measurement using electron microscopy. However, other indirect methods of determining crystal size are available and can be useful in differentiating between small crystal materials, especially when no exact size can be assigned visually as the result of size polydispersity, irregular/non-uniform shape and/or extensive crystal intergrowth. For example, the nitrogen adsorption/desorption isotherm showing the amount of nitrogen adsorbed by a solid at 77° K as the function of relative parti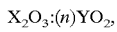al pressure $p/p_0$ can be used to gauge and compare average crystal size of materials. The isotherm can be used to calculate apparent internal (zeolite) and external (mesoporous) surface area, ZSA and MSA, respectively, of the crystals. Increasing MSA indicates decreasing crystal size. At low nitrogen partial pressures the isotherm tracks filling of the zeolite micropores but at higher relative partial pressures, i.e. 0.4–0.7 for ZSM-5, the slope of the isotherm reflects the crystal size. This latter approach is usefull when ambiguity in determining the MSA/ZSA split may arise.

According to the invention, a novel form of ZSM-5 has now been produced with a combination of an unusually low silica to alumina molar ratio and a very small crystal size.

It is to be appreciated that, although ZSM-5 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

SUMMARY OF THE INVENTION

In one aspect, the invention resides in a synthetic porous crystalline material having the structure of ZSM-5 and a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than 25, and wherein the slope of the nitrogen sorption isotherm of the material at a partial pressure of nitrogen of 0.4 to 0.7 and a temperature of 77° K is greater than 30.

Preferably, the slope of the nitrogen sorption isotherm at said partial pressure of nitrogen of 0.4 to 0.7 and said temperature of 77° K is greater than 50.

Preferably, n is about 15 to about 20.

Preferably, the crystalline material has an alpha value in excess of 1300.

Preferably, the crystalline material has a BET surface area in excess of 400 $m^2/g$ in which the MSA (mesoporous surface area) is greater than 45 $m^2/g$ and the ratio of the ZSA (zeolite surface area) to MSA is less than 7.

In a further aspect, the invention resides in a hydrocarbon conversion process employing a catalyst comprising the synthetic porous crystalline material of said one aspect of the invention.

Preferably, the hydrocarbon conversion process is xylene isomerization or toluene disproportionation.

BRIEF DESCRIPTION OF THE DRAWINGS

FIG. 1 shows the nitrogen adsorption isotherms for ZSM-5 produced according to Example 1 and for a variety of conventional ZSM-5 materials of different crystal size labelled Catalysts 1–4.

DESCRIPTION OF SPECIFIC EMBODIMENTS

The present invention provides a novel form of high activity, small crystal ZSM-5 having a composition involving the molar relationship:

$X_2O_3:(n)YO_2$, wherein X is a trivalent element, such as aluminum, boron, iron and/or gallium, preferably aluminum; Y is a tetravalent element such as silicon and/or germanium, preferably silicon; and n is less than about 25, preferably 15–20.

The small crystal size of the novel ZSM-5 of the invention is manifested in a unique nitrogen sorption isotherm wherein the slope of the isotherm at a partial pressure of nitrogen of 0.4 to 0.7 and a temperature of 77° K is greater than 30. In contrast, the slope of the nitrogen adsorption isotherm of conventional ZSM-5 materials within the same partial pressure range and at the same temperature varies from <10 for crystal sizes >1 micron to 10–15 for crystal sizes between 0.2–0.5 micron and 20–25 for conventional small crystal materials having a size less than 0.1 micron.

Measurement of nitrogen sorption isotherms and of BET, MSA and ZSA surface areas is well known in the art, e.g. as ASTM Method D 4365-95 "Standard Test Method for Determining Micropore Volume and Zeolite Area of Catalysts".

The small crystal ZSM-5 of the invention also exhibits a BET surface area in excess of 400 $m^2/g$ in which the MSA (mesoporous surface area) is greater than 45 $m^2/g$, preferably greater than 75 and more preferably at least 100, and in which the ratio of the ZSA (zeolite surface area) to MSA is less than 8, and more preferably is less than 5. In contrast, the MSA for conventional ZSM-5 materials varies between 10 and 40 $m^2/g$ and the ratio of the ZSA to MSA varies between 9 and 40.

The small crystal size of the ZSM-5 of the invention can also be deduced from other sorption measurements, for example by measuring the rate of sorption of 2,2-dimethylbenzene at 120° C. and 60 torr (8 kPa) hydrocarbon pressure. Based on such sorption measurements, the Diffusion Parameter, $D/r^2$ wherein D is the diffusion coefficient ($cm^2/sec$) and r is the crystal radius (cm), can be derived provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967. The small crystal ZSM-5 of the invention will normally have a Diffusion Parameter, $D/r^2$, of at least $2000 \times 10^{-6}$ and preferably at least $2500 \times 10^{-6}$.

The small crystal ZSM-5 of the invention will normally be comprised of crystals of which at least 50% by weight have dimensions less than 0.05 micron as measured by transmission electron microscopy (TEM).

Since the small crystal ZSM-5 of the invention has a uniquely low silica/alumina molar ratio (that is high aluminum content), the hydrogen form of the material has an extremely high catalytic activity. Catalytic activity of zeolites, such as ZSM-5, is typically measured by Alpha Value, which compares the catalytic cracking activity of the catalyst (rate of normal hexane conversion per volume of catalyst per unit time) with the activity of a standard silica-alumina cracking catalyst. The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), the entire contents of which are incorporated herein by reference. The experimental conditions of the test used herein include a constant temperature of 538° C. and a variable flow rate as described in detail in the *Journal of Catalysis*, Vol. 61, p. 395. In the hydrogen form, the small crystal ZSM-5 of the invention has an Alpha Value in excess of 1000 and preferably in excess of 1300.

Small crystal high activity ZSM-5 of the invention is synthesized using an amorphous silica-alumina having a silica/alumina molar ratio of 10:1 to 25:1 as a raw material either with or without additional silica and alumina sources. Suitable amorphous silica-alumina materials are conveniently prepared by co-precipitation from soluble silica and alumina sources followed by suitable washing and cation exchange with an ammonium salt. They are also available from commercial suppliers like WRGrace. The reaction mixture may be totally inorganic but more preferably contains n-propylamine as an organic directing agent (R). More specifically the reaction mixture has a composition, expressed in terms of mole ratios of oxides, as follows:

| Component | Useful | Preferred |
|---|---|---|
| $SiO_2/Al_2O_3$ | 10–25 | 15–20 |
| $H_2O/SiO_2$ | 5–30 | 8–20 |
| $R/SiO_2$ | 0–1.0 | 0–0.4 |
| $M/SiO_2$ | 0.01–0.5 | 0.15–0.2 | where M is an alkali or alkaline earth metal.

The synthesis method of the invention functions with or without added nucleating seeds. In a preferred embodiment, the reaction mixture contains 0.05–5 wt % nucleating seeds.

Crystallization is carried out under either stirred or static conditions at a temperature of 100 to 200° C., preferably 120 to 170° C., for 6 hours to 10 days and the resultant ZSM-5 crystals are separated from the mother liquor and recovered.

When used as a catalyst, it may be desirable to incorporate the small crystal ZSM-5 of the invention with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided ZSM-5 material and inorganic oxide matrix vary widely, with the ZSM-5 content ranging from about 1 to about 90% by weight and more usually, particularly when the composite is prepared in the form of beads, in the range of about 2 to about 80 wt. % of the composite.

The small crystal ZSM-5 of the invention is useful as a catalyst in hydrocarbon conversion reactions where high activity and/or rapid diffusion of reactants and/or products out of the zeolite pores is important. For example, the ZSM-5 of the invention is useful as a catalyst for disproportionation of toluene and for the liquid or supercritical phase isomerization of xylenes under conditions including a temperature of from about 300 to 600° C., a pressure of from about 1 to 100 atmospheres (about 100 to 10,000 kPa), a weight hourly space velocity (WHSV) of about 0.5 to 100 $hr^{-1}$, and a hydrogen/hydrocarbon mole ratio of 0 (no added hydrogen) to about 10. Where the catalyst is used in xylene isomerization, the xylene isomerization step could be the second stage in a two stage process in which a $C_8$ aromatics stream was initially subjected to an ethylbenzene conversion step.

In order to more fully illustrate the nature of the invention and the manner of practicing same, the following examples are presented.

EXAMPLE 1

A synthesis mixture was produced from 320 g of water, 37.5 g of amorphous silica-alumina having silica/alumina molar ratio of 10:1 (as supplied by WRGrace), 24 g of HiSil 233, 10 g of 50% NaOH solution, 7 g of N-propylamine and 3 g of ZSM-5 seeds. The mixture was reacted at 154° C. (310° F.) in a Parr autoclave with stirring at 200 RPM. The crystallization was interrupted after 24 and 48 hr. for sampling, and 2 g of 50% NaOH was added following the latter. The product obtained after 72 hr. synthesis was filtered, washed with water and dried at 100° C. The solid was identified as ZSM-5 with a small amount of crystalline impurity using powder X-ray diffraction.

The as-synthesized material was converted into the hydrogen form by multiple ion exchange with ammonium chloride solution at 82° C. (180° F.), followed by drying in an oven and calcination at 540° C. in air for 6 hours. The resultant HZSM-5 had a silica/alumina molar ratio of about 15:1, an Alpha Value of 1365, and a BET surface area of 415 $m^2/g$ (290 zeolite surface area and 125 matrix surface area). The small crystal size of the material was demonstrated by TEM (which indicated a crystal size<0.05 $\mu$) and confirmed by a high $D/r^2$ parameter for 2,2-dimethylbenzene of about $3700\times10^{-6}$.

The nitrogen adsoption isotherm of the HZSM-5 of Example 1 is plotted in FIG. 1 against those of the following conventional ZSM-5 materials:

1. ZSM-5 with an average crystal size of 2 microns.
2. Non-organic ZSM-5 with a crystal size of 0.2–0.5 microns.
3. ZSM-5 with a crystal size less than 0.1 micron synthesized according to the method described in U.S. Pat. No. 3,926,782.
4. ZSM-5 with a crystal size less than 0.1 micron synthesized according to the method described in U.S. Pat. No. 5,369,071.

It will be seen from FIG. 1 that in the $P/P_0$ range of 0.4–0.7, the isotherm for the ZSM-5 of Example 1 had a slope 88.5 as compared with values for the conventional materials of 9.4 (material 1 above), 12.3 (material 2 above), 23.5 (material 3 above) and 25.8 (material 4 above).

EXAMPLE 2

A synthesis mixture was prepared from 250 g of water, 80 g of amorphous silica-alumina having a silica/alumina molar ratio of 25:1 (as supplied by WR Grace), 4 g of sodium aluminate solution (19.5% $Na_2O$, 25.5% $Al_2O_3$), 10 g of 50% NaOH solution and 3 g of ZSM-5 seeds. The mixture was reacted at 160° C. (320° F.) in a Parr autoclave with stirring at 100 RPM for 168 hr (with interruptions for sampling). The product was filtered, washed with water and dried at 120° C. (250° F.).

The as-synthesized material was converted into the hydrogen form by multiple ion exchange with ammonium chloride solution at 82° C. (180° F.), followed by drying in the oven and calcination at 540° C. in air for 6 hours. The resultant HZSM-5 was found to have a silica/alumina molar ratio of 19:1, an Alpha Value of 1750, a BET surface area of 412 $m^2/g$ (364 zeolite surface area and 48 matrix surface area), and a $D/r^2$ parameter for 2,2-dimethylbenzene of about $2500\times10^{-6}$.

EXAMPLE 3

A synthesis mixture was prepared from 250 g of water, 80 g of amorphous silica-alumina having a silica/alumina molar ratio of 25:1 (as supplied by WRGrace), 6 g of sodium aluminate solution (19.5% $Na_2O$, 25.5% $Al_2O_3$), 10 g of 50% NaOH solution and 3 g of ZSM-5 seeds. The mixture was reacted at 160° C. (320° F.) in a Parr autoclave with stirring at 100 RPM for 192 hr (with interruptions for sample withdrawal). The product was filtered, washed with water and dried at 120° C. (250° F.).

The as-synthesized material was converted into the hydrogen form as in the previous Examples and the resultant HZSM-5 had a silica/alumina molar ratio of 19:1, an Alpha Value of 1528 and a BET surface area of 398 $m^2/g$ (346 zeolite surface area and 53 matrix surface area).

EXAMPLE 4

The HZSM-5 of Example 1 (Catalyst C in Table 1 below) was pelletized, crushed and sized to 12/40 mesh and then used to effect liquid phase isomerization of a mixed xylene feed having the composition given in Table 1 below. For comparison, the same feed was isomerized using catalysts prepared from the conventional ZSM-5 materials (3) and (2) in Example 1 and referred to as Catalysts A and B respectively in Table 1.

In each case testing was conducted in an automated unit with on-line sampling using a 0.375 inch (0.95 cm) diameter stainless steel tube reactor into which was loaded 1 gm of the catalyst with sand as an inert packing material. The reactor was pressurized with nitrogen to 550 psig (3890 kPa) and heated to 560° F. (293° C.) under flowing nitrogen. After introduction of the liquid feed to the reactor, all gas flow was stopped. Conditions for these runs were 8.8 WHSV, 550 psig (3890 kPa), and 0 H2/HC. Temperature was varied to effect xylene isomerization. Results are tabulated below.

TABLE 1

| CATALYST | Feed | Catalyst A | Catalyst B | Catalyst C |
|---|---|---|---|---|
| Temperature ° F. (° C.) | | 563 (295) | 563 (295) | 491 (255) |
| Yields (wt %) | | | | |
| Toluene | 0.6 | 0.9 | 1.1 | 0.8 |
| Ethylbenzene | 0.3 | 0.3 | 0.3 | 0.3 |
| Total Xylenes | 98.4 | 97.8 | 97.6 | 98.2 |
| Total C9+ | 0.7 | 1.0 | 1.1 | 0.7 |
| Xylene loss, wt % | | 0.5 | 0.8 | 0.2 |
| P-xylene/Total Xylene, wt % | 12.6 | 23.4 | 23.1 | 23.3 |
| Para approach to equilibrium, wt % | | 95.0 | 92.6 | 92.5 |

The results given in Table 1 show that the ZSM-5 of the invention (Catalyst C) was 70° F. (40° C.) more active than either the high activity preparation (Catalyst B) or the "small crystal" preparation (catalyst A). Further, utilizing the catalyst of the present invention results in lower xylene loss.

EXAMPLE 5

Catalyst C of Example 4 was used to effect disproportionation of a toluene feed at conditions including a temperature of 800° F. (427° C.), a pressure of 400 psig (2860 kPa), WHSV of 9.2 hr$^{-1}$ and a H2/HC (molar) of 1. The product yields were as follows:

| | |
|---|---|
| C5- | 1.0 wt % |
| Benzene | 19.5 wt % |
| Ethylbenzene | 0.5 wt % |
| P-xylene | 5.7 wt % |
| M-xylene | 12.4 wt % |
| O-xylene | 5.5 wt % |
| C9+ | 3.0 wt % |
| Para Selectivity | 24.2 |
| Toluene conversion | 48 |
| Benzene/xylene (molar) | 1.12 |

What is claimed is:

1. A hydrocarbon conversion process comprising the step of contacting a hydrocarbon feedstock with a catalyst comprising a synthetic porous crystalline material having the structure of ZSM-5 and a composition involving the molar relationship:

$$X_2O_3:(n)YO_2,$$

wherein X is a trivalent element, Y is a tetravalent element, and n is less than 20, and wherein the slope of the nitrogen sorption isotherm of the material at a partial pressure of nitrogen of 0.4 to 0.7 and a temperature of 77° K is greater than 30.

2. The hydrocarbon conversion process of claim 1 wherein the hydrocarbon feedstock contains aromatic compounds.

3. The hydrocarbon conversion process of claim 2 wherein the process includes toluene disproportionation.

4. The hydrocarbon conversion process of claim 3 which comprises process conditions which include a temperature of from about 300 to 600° C., a pressure of from about 1 to 100 atmospheres (about 100 to 10,000 kPa), a weight hourly space velocity (WHSV) of about 0.5 to 100 hr$^{-1}$, and a hydrogen/hydrocarbon mole ratio of 0 (no added hydrogen) to about 10.

5. The hydrocarbon conversion process of claim 2 wherein the process includes xylene isomerization.

6. The hydrocarbon conversion process of claim 5 which comprises process conditions which include a temperature of from about 300 to 600° C., a pressure of from about 1 to 100 atmospheres (about 100 to 10,000 kPa), a weight hourly space velocity (WHSV) of about 0.5 to 100 hr$^{-1}$, and a hydrogen/hydrocarbon mole ratio of 0 (no added hydrogen) to about 10.

7. The hydrocarbon conversion process of claim 2 wherein the process includes liquid phase xylene isomerization.

8. The hydrocarbon conversion process of claim 2 wherein the process includes supercritical phase xylene isomerization.

9. The hydrocarbon conversion process of claim 1 wherein said slope of the nitrogen sorption isotherm at said partial pressure of nitrogen of 0.4 to 0.7 and a temperature of 77° K is greater than 50.

10. The hydrocarbon conversion process of claim 1 wherein said n is about 15 to about 20.

11. The hydrocarbon conversion process of claim 1 wherein said material has a mesoporous surface area (MSA) greater than 45 m$^2$/g.

12. The hydrocarbon conversion process of claim 1 wherein said material has a ratio of zeolite surface area (ZSA) to MSA of less than 7.

13. The hydrocarbon conversion process of claim 1 wherein said material has an Alpha Value in excess of 1300.

14. The hydrocarbon conversion process of claim 1 wherein X is aluminum and Y is silicon.

* * * * *